US010332631B2

(12) United States Patent
Miller et al.

(10) Patent No.: US 10,332,631 B2
(45) Date of Patent: Jun. 25, 2019

(54) INTEGRATED MEDICAL PLATFORM

(71) Applicant: Seven Medical, Inc., Toronto (CA)

(72) Inventors: Jonathan David Miller, Austin, TX (US); L. James Valverde, Jr., Washington, DC (US); Harold Roy Miller, Toronto (CA)

(73) Assignee: Seven Medical, Inc., Toronto (CA)

( * ) Notice: Subject to any disclaimer, the term of this patent is extended or adjusted under 35 U.S.C. 154(b) by 0 days.

(21) Appl. No.: 14/793,189

(22) Filed: Jul. 7, 2015

(65) Prior Publication Data

US 2017/0011183 A1     Jan. 12, 2017

(51) Int. Cl.
*G16H 50/20* (2018.01)
*G06F 17/24* (2006.01)
*G06F 17/27* (2006.01)
*G16H 10/60* (2018.01)

(52) U.S. Cl.
CPC .......... *G16H 50/20* (2018.01); *G06F 17/241* (2013.01); *G06F 17/278* (2013.01); *G06F 17/2785* (2013.01); *G16H 10/60* (2018.01)

(58) Field of Classification Search
CPC ........................................ G06Q 50/22–50/24
USPC ....................................................... 705/2–3
See application file for complete search history.

(56) References Cited

U.S. PATENT DOCUMENTS

| 2007/0106536 A1* | 5/2007 | Moore | G06F 19/325 705/3 |
| 2009/0005650 A1* | 1/2009 | Angell | A61B 5/411 600/300 |
| 2010/0324927 A1* | 12/2010 | Tinsley | G06F 19/325 705/2 |
| 2015/0193583 A1* | 7/2015 | McNair | G06F 19/00 705/2 |
| 2015/0356262 A1* | 12/2015 | Liebovitz | G16H 50/20 702/19 |

* cited by examiner

*Primary Examiner* — Michael Tomaszewski
(74) *Attorney, Agent, or Firm* — Carr & Ferrell LLP

(57) ABSTRACT

Provided is a system for automated medical decision-making. The system may include a first parser configured to parse text associated with medical information sources to obtain medical information and a second parser configured to parse patient data to obtain processed patient data. A processor, in communication with the first parser and the second parser, is configured to structure the medical information to form structured medical metadata in an intelligent medical database. Based on the structured medical metadata, the processor creates a causal network and receives the patient data from patient data sources. When the patient data is parsed by the second parser and the processed patient data is obtained, the processor maps the processed patient data against the causal network and generates the medical decision for the patient based on the mapping.

18 Claims, 10 Drawing Sheets

INTEGRATED MEDICAL PLATFORM

TECHNICAL FIELD

The application relates generally to the field of medicine and, more specifically, to automated medical decision-making.

BACKGROUND

Recent decades have seen considerable advancements in bio-informatics and artificial intelligence in medicine. Various computerized expert systems have been developed to collate medical data with varied diseases to aid physicians in diagnosing and prescribing treatments for their patients. Numerous systems exist that provide diagnoses or suggest treatment strategies.

However, the knowledge base for medicine is vast and varied. There are disparate libraries, books, articles, and papers that describe various aspects of medical knowledge written in natural languages. Even where information about a specific disease is collated and provided in a comprehensive document, there is no mechanism by which this document can be immediately utilized to diagnose a disease without a careful review.

The ability to make intelligent conclusions based on the available knowledge is a difficult task, owing to the complex informatics, inferential, and value-laden nature and character of medical decision-making.

SUMMARY

Provided are methods and systems for automated medical decision-making. In general, the disclosed methods and systems are related to data parsing and automated knowledge discovery, bioinformatics ontology, diagnostic reasoning coupled with machine learning, decision-making, and risk-based evaluation. In the present disclosure, an integrated medical platform is provided that assists, particularly in an online environment, a patient or attending physician in determining possible diagnoses with accompanying statistical likelihoods, complete with recommended treatment and patient management plans. Additionally, the disclosed methods and systems can facilitate self-monitoring and management of chronic health conditions of the patient.

In certain embodiments, a method for providing automated medical decision-making involves parsing, by a first parser, text associated with one or more medical information sources to obtain medical information, and structuring the medical information to form structured medical metadata in an intelligent medical database. The structured medical metadata may comprise elements and relationships between the elements. The elements of the structured medical metadata may include one or more of the following: a disease, a state, a cause, a symptom, a treatment, a test, an effect, an outcome, or an outlier. A causal network may be created based on the structured medical metadata. The causal network may include a topological space with nodes and links between the nodes, wherein the nodes represent the elements of the structured medical metadata, and the links represent the relationships between the elements. The relationships between the elements of the structured medical metadata may be weighted statistically based on the patient data. The method may further involve receiving patient data from one or more patient data sources; parsing, by a second parser (e.g., alternative bio-informatics ontology), the patient data to obtain processed patient data; mapping the processed patient data against the causal network; and, based on the mapping, providing automated medical decision-making, such as generating a medical decision for a patient.

In certain embodiments, the first parser and the second parser may include grammar independent natural language parsers configured to retrieve, interpret, and collate the medical information from the one or more medical information sources.

In certain embodiments, the medical information may be obtained from the one or more medical information sources using a metadata dictionary and/or pattern recognition. The metadata dictionary may include an equivalence class of terms and phrases associated with a medical lexicon. The metadata dictionary may be captured using bioinformatics ontology.

In certain embodiments, the patient data may be processed using inference model and pattern recognition. The patient data may include patient input in the form of a natural language. The patient input may include text or speech converted into text.

BRIEF DESCRIPTION OF THE DRAWINGS

Embodiments are illustrated by way of example and not limitation in the figures of the accompanying drawings.

DETAILED DESCRIPTION

Figure 1:
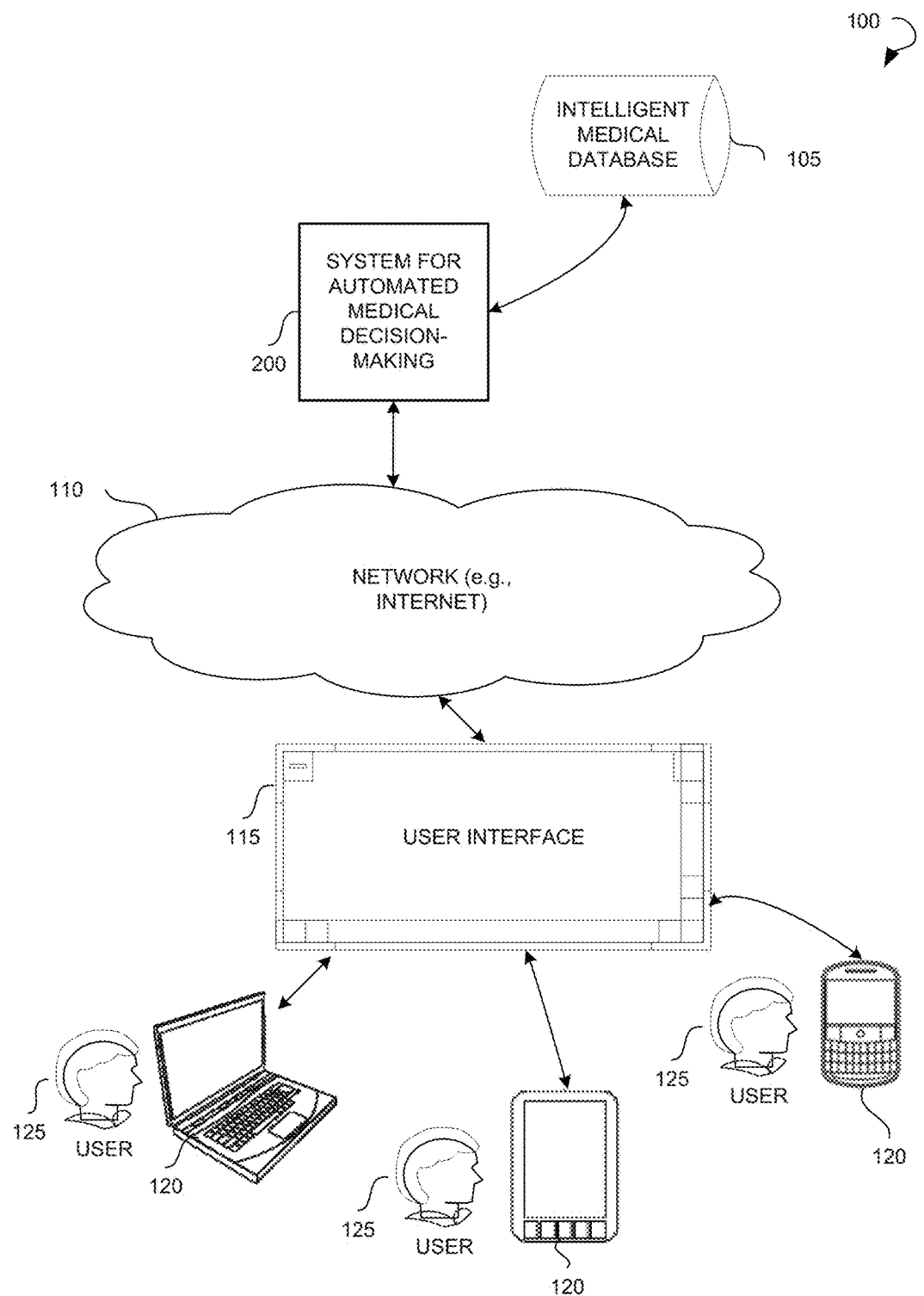
FIG. 1 illustrates a block diagram showing a sample environment within which methods and systems for automated medical decision-making may be implemented.

In the following description, numerous specific details are set forth in order to provide a thorough understanding of the presented concepts. The presented concepts may be practiced without some or all of these specific details. In other instances, well known process operations have not been described in detail so as to not unnecessarily obscure the described concepts. While some concepts will be described in conjunction with the specific embodiments, it will be understood that these embodiments are not intended to be limiting.

Systems and methods described herein may allow a user of a computing device, such as a desktop computer, laptop computer, cell phone, smart phone, or the like, to receive a diagnosis and treatment option, health conditions of a certain person, medical history, and other (possibly relevant) environmental factors. The diagnosis and treatment option may be provided by an integrated medical platform. The integrated medical platform may be part of the system for automated medical decision-making. The integrated medical platform may be based on inference and statistics instead of, or in addition to, pathology or clinical gestalt. The integrated medical platform may include two natural language parsers, each with unique methods and functions. The first (backend) parser may be responsible for reading various medical literature (journals, standards, and the like) and building backend structures that form the framework of the system intelligence. The second (frontend) parser may read electronic medical records (EMRs) and parse patient input, taking pertinent information and feeding it to the backend structures. These structures may include subsystems of an intelligent medical database, which stores all relevant information pertaining to various diseases in a well-structured way.

The system may further comprise a causal network, which connects various symptoms, treatments, and diseases in ways that a database table could not have possibly achieved, and in more ways than any doctor could remember at any given moment. There may also be provided two distinct inference models: one inference model may be used with the second parser to help in determining a meaning of the patient input, and the other, with the first parser, makes use of the statistical data available to establish a diagnosis. These subsystems may feed data into the integrated medical platform that provides, to a patient or attending physician, a set of possible diagnoses with accompanying statistical likelihoods, complete with recommended treatment, patient management plans, and the ability to project and/or track a treatment prognosis of a patient. These subsystems can be assisted by a QALY (quality-adjusted-life-years) valuation component.

In certain example embodiments, there may be provided several derivative products that emerge as a direct result of the technology described in the present application, among which are medical/life insurance related models, various data products (efficiency of treatment options, comparative analysis between drugs), specific patient-centric forecast models, unique scheduling algorithms (obtaining tests needed for diagnosis before visiting a doctor), and unique advertising for drug companies, as well as doctor tracking. For example, doctors whose recommendations consistently contradict the recommendations of the system, resulting in patients with treatable illnesses returning more frequently than they should, can be reviewed by the patient and employing clinics.

The integrated medical platform of the present technology may have several advantages: 1) all potential diseases associated with any patient and set of symptoms are considered; 2) the probability of each disease is calculated; 3) outliers, in particular dangerous ones, are identified; 4) missed questions with respect to symptoms are automatically asked to render the best statistical diagnosis possible; 5) tests that enhance the probability of a condition, sometimes in advance of a visit of a doctor; 6) main disadvantages of clinical gestalt are obviated; 7) the entirety of medical clinical gestalt is always considered; 8) efficiency in traversing the network as opposed to reading through tables; 9) immediate availability of probability distributions assigned to information.

The integrated medical platform may receive the information from the first and second parsers, identify medical metadata and phrases, and insert the metadata and phrases into the causal network, typically, as symptoms, if coming directly from a patient. If the information is coming from the EMR of the patient, the integrated medical platform may parse the information and create a clinical gestalt of the patient as a subnet of the causal network. The subnet of the causal network may comprise nodes that represent diseases, symptoms, treatments, states associated with the patient, and links between the nodes that are directed dependencies. The links in the causal network subnet may be statistically weighted, and these weights may be specific to the patient. The second parser may feed symptoms and other data to the integrated medical platform. The integrated medical platform may map the symptoms against the causal network and identify the entire subnet for these symptoms. This approach will allow recognizing a set of diseases, conditions, and states together with corresponding probabilities. Probability distributions may be assigned dynamically to a patient, based on the characteristics of the patient, the probability distributions of the causal network, and the statistical database for the patient population.

The integrated medical platform may provide the capability of traversing the causal network in multiple directions or paths, thereby identifying additional or corroborating symptoms, conditions, treatments, and states (amongst other relationships) along with corresponding likelihoods. In particular, for each potential disease or condition identified, associated diseases, symptoms and outcomes can be calculated and likelihood functions assigned (e.g., the likely condition of the patient and the likely responses to a given set of treatment options). If the likelihood falls below a certain threshold, the integrated medical platform may not render a medical decision or diagnosis.

The integrated medical platform may build a list of diseases or conditions and refine a medical decision or conclusion by asking questions or by requesting specific tests. This refinement, or set of refinements, may be established to eliminate dangerous outcomes, outliers, and to put aside other tests or investigations that do not increase the likelihood of the diagnosis.

A medical decision may be essentially a subnet of the causal network with a probability distribution for the subnet. The subnet may contain multiple diagnoses, which may be similar or different. The medical decision may be the most likely set of concurrent discrete paths in the subnet. The integrated medical platform may be developed with several unique methods for understanding severity and acuteness of patient conditions. Severity and acuteness of patient conditions has always been difficult to establish due to the subjectivity of the patient response and the absence of reliable measurements.

The integrated medical platform may have additional capability for interpreting pain levels from the perspective of a disease or condition. For example, if the pain is likely associated with appendicitis, the integrated medical platform may have many options for the location(s) and acuteness of the pain.

Having determined a diagnosis in the earlier steps, the system for automated medical decision-making may now turn to patient care. Today, when a doctor prescribes a treatment that works, the patient does not return. If, on the other hand, the treatment does not work, the patient will be back and his condition may even get worse.

The system should know, within statistical boundaries, how the patient is responding to medication/care over the course of the treatment. By getting constant feedback from the patient over the course of his/her regimen, doctors, and patients can quickly determine whether the correct medical decision and/or treatment option was made. If, for example, a patient who apparently suffers from asthma at night only was placed on a treatment plan for acid reflux disease, and after a week the patient no longer experiences any improvements, the system may reevaluate the medical decision/treatment and adjust accordingly.

Moreover, the system may be able to provide the patient with a prognosis within statistical boundaries of the results, risks, and consequences of treatment or lack thereof, thus allowing the patient/doctor to act on a full knowledge set and come to a conclusion about the best way forward for the patient given his or her circumstances.

Using the causal network and corresponding probability assignments, the system allows predicting future patient gestalts, identifying diseases and treatments, progression and consequences the diseases will have over time for a patient, and possible treatments. Using the causal network and the statistical data from patient population, more accurate prediction of drug use and other treatment options may be made. Additionally, mortality and morbidity predictions, with and without treatment, may be made. Screening requirements for individuals within the patient population may be determined from the statistical tables and preventative measures taken.

Referring now to the drawings, FIG. 1 shows an architecture 100 that may include a network 110, client devices 120, users 125, a user interface 115, a system for automated medical decision-making 200, and an intelligent medical database 105 which is part of the system for automated medical decision-making 200. The network 110 may include the Internet or any other network capable of communicating data between devices. Suitable networks may include or interface with any one or more of, for instance, a local intranet, a PAN (Personal Area Network), a LAN (Local Area Network), a WAN (Wide Area Network), a MAN (Metropolitan Area Network), a virtual private network (VPN), a storage area network (SAN), a frame relay connection, an Advanced Intelligent Network (AIN) connection, a synchronous optical network (SONET) connection, a digital T1, T3, E1 or E3 line, Digital Data Service (DDS) connection, DSL (Digital Subscriber Line) connection, an Ethernet connection, an ISDN (Integrated Services Digital Network) line, a dial-up port such as a V.90, V.34 or V.34bis analog modem connection, a cable modem, an ATM (Asynchronous Transfer Mode) connection, or an FDDI (Fiber Distributed Data Interface) or CDDI (Copper Distributed Data Interface) connection. Furthermore, communications may also include links to any of a variety of wireless networks, including WAP (Wireless Application Protocol), GPRS (General Packet Radio Service), GSM (Global System for Mobile Communication), CDMA (Code Division Multiple Access) or TDMA (Time Division Multiple Access), cellular phone networks, GPS (Global Positioning System), CDPD (cellular digital packet data), RIM (Research in Motion, Limited) duplex paging network, Bluetooth radio, or an IEEE 802.11-based radio frequency network. The network 110 can further include or interface with any one or more of an RS-232 serial connection, an IEEE-1394 (Firewire) connection, a Fiber Channel connection, an IrDA (infrared) port, a SCSI (Small Computer Systems Interface) connection, a USB (Universal Serial Bus) connection or other wired or wireless, digital or analog interface or connection, mesh or Digi® networking. The network 110 may include a network of data processing nodes that are interconnected for the purpose of data communication.

The client devices 120, in some example embodiments, may include a Graphical User Interface (GUI) for displaying the user interface 115. In a typical GUI, instead of offering only text menus or requiring typed commands, the system presents graphical icons, visual indicators, or special graphical elements that may be utilized to allow users 125 to interact with the user interface 115. The client devices 120 may be configured to utilize icons used in conjunction with text, labels, or text navigation to fully represent the information and actions available to users.

The client devices 120 may include a desktop computer, laptop computer, cell phone, smart phone, gaming device, a wearable device, or the like. The user 125, in some example embodiments, is a person interacting with the user interface 115 via the client devices 120. The user 125 may experience certain symptoms and be seeking medical care. The user 125 may access the system for automated medical decision-making 200 through a client device 120 and the Internet. Alternatively, the user 125 may access the system 200 via a mobile or another device. The user 125 may periodically interact with the system for automated medical decision-making 200 and present information to the system for automated medical decision-making 200. This information may be stored in an intelligent medical database 105 and include medical knowledge relating to diseases, states, causes, symptoms, and the like. All medical knowledge may be expressed as the sum of a set of binary relationships between elements of the intelligent medical database 105 including but not limited to: causes, symptoms, treatments, tests, effects, outcomes, diseases, states, and the like, wherein relations between the elements may include but be not limited to: causes, effects, conditional likelihoods, and the like. These relationships may be further qualified by sex, age, and the like, which may include various qualities and quantities associated with a patient. For example, smoking has a causal relationship to emphysema, gastro-esophageal reflux disease (GERD), and asthma. Similarly, a postal code of a patient may have a conditional likelihood relationship with breast cancer. The intelligent medical database 105 is a set of binary relationships that forms a cover of existent (known) medical knowledge and may include pathological relationships if desired.

Once the data obtained from the user 125 is processed, the user 125 may be provided with information concerning his or her condition, and a recommendation may be made with respect to further medical care.

Figure 2:
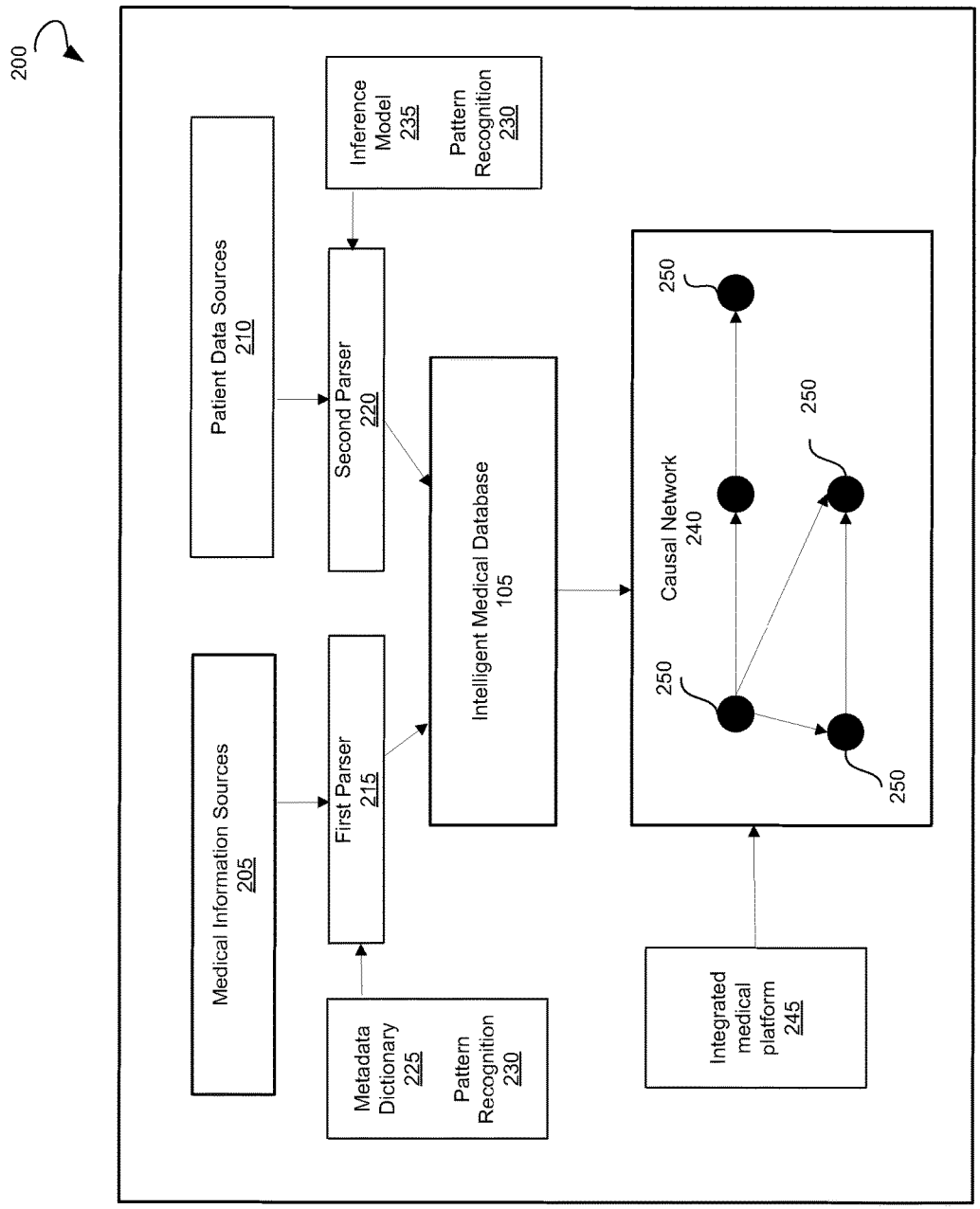
FIG. 2 shows a block diagram illustrating a sample system for automated medical decision-making.

FIG. 2 is a block diagram illustrating a sample system for automated medical decision-making 200, in accordance with an example embodiment. The sample system 200 may comprise a processor (not shown). The processor may be configured to parse text associated with one or more medical information sources 205 to obtain medical information, structure the medical information to form structured medical metadata in an intelligent medical database 105, and create a causal network 240 based on the structured medical metadata. The structured medical metadata may comprise elements and relationships between the elements.

The processor may be further configured to receive patient data from one or more patient data sources 210, parse the patient data to obtain processed patient data, and map the processed patient data against the causal network 240.

Finally, the processor may be configured to generate a medical decision for a patient based on the mapping of the processed patient data against the causal network.

The system 200 may also comprise a first parser 215 and a second parser 220. The first parser 215 may be used to parse text associated with one or more medical information sources 205 to obtain medical information. The first parser 215 may be further configured to create one or more backend structures based on the obtained medical information. The one or more backend structures may form a framework against which mapping is performed. The second parser 220 may be used to parse patient data from one or more patient data sources 210 to obtain processed patient data.

In certain example embodiments, the first parser 215 may use equivalence classes of medical terms and phrases found in a metadata dictionary 225. The first parser 215 may then use the metadata dictionary 225, along with pattern recognition 230, to pick up pertinent medical information and map the information against the backend structures, thus populating the intelligent medical database 105 with various medical terms and phrases, such as, for example, names of diseases. These medical terms and phrases may be referred to as elements of the intelligent medical database 105.

In certain example embodiments, the first parser 215 may build relationships between the elements of the intelligent medical database 105. For example, the first parser 215 may build a relationship between the two diseases asthma and GERD in the intelligent medical database 105. The first parser 215 may be concerned with mapping medical articles, doctor inputs, and medical journals to the intelligent medical database 105. Having predefined the concept of a symptom, the first parser 215 may, using pattern recognition 230, establish the meaning of the word or phrase and appropriately place the word or phrase within the structure of the intelligent medical database 105.

The medical metadata may be constantly updated and appended. The first parser 215 may read, decode, and update the medical metadata to reflect the additions and modifications as new journals are published and accepted by the medical community, new drugs are developed, diseases discovered, treatment data changes, and new standards are constructed. Relationships between diseases previously thought as unrelated may be formalized, and the medical metadata may be updated to reflect these changes. The entire process may be auditable at various points by medical professionals.

In certain example embodiments, the second parser 220 may use an inference model 235, medical vocabulary, and pattern recognition 230 to obtain important information from a patient input and disregard the unimportant information. It is important to note that the second parser 220 is not a grammar-based parser. This is imperative for the system for automated medical decision-making 200 to provide clear reports because patients and doctors could be rightfully concerned about a condition and reports that are not communicated clearly. The system 200 can be translated easily into any language without a complete rewrite of the parser logic.

The second parser 220 may take symptoms, diseases, and medical histories (such as electronic medical records), and build a use case for a patient, prompting for any information that requires attention (for example sex, age, and the like). This information may provide the context for the responses with appropriate pattern recognition and keywords that are acceptable as a response. The second parser 220 may be provided with intelligence to understand the relevance of phrases submitted. For example, if someone inputs that he or she is "feeling it's difficult to breathe," the second parser 220 has this phrase listed as a symptom. The second parser 220 may then pick up this phrase and drop it into a symptom node 250 in a causal network 240, rapidly traversing the causal network 240 to ascertain all possible diagnoses.

The second parser 220 may be aided by an inference model 235. If a patient inputs "my heart aches for my lost love," for example, the system 200 will disregard the possible romantic context and infer "the patient is having chest pains."

The second parser 220 may take natural language and identify what the patient is describing about himself, his symptoms, and the severity of these symptoms based on pattern recognition 230 artificial intelligence. There is no grammar base for the parsing, and the system, apart from the metadata and phrase library, is language independent.

The second parser 220 may feed the symptoms and other data to an integrated medical platform 245. The integrated medical platform 245 may map these symptoms against the causal network 240 and identify a subnet for these symptoms. The integrated medical platform 245 may recognize a set of diseases, conditions and states, together with corresponding probabilities.

The integrated medical platform 245 may include a list of questions and, possibly, tests. For each specific case, the integrated medical platform 245 may formulate and immediately ask questions to better rank the possibilities for each disease. Responses may be refactored into a medical decision and a ranked assessment may be made.

From the initial list with the corresponding probability distribution and ranking, additional symptoms may be identified for each disease or condition on the list. The integrated medical platform 245 may determine a new set of questions and tests it needs in order to accomplish several things, such as: 1) identify or eliminate any serious conditions (sometime outliers); 2) refine the likelihood of any of the ranked conditions identified; 3) shorten the list of possibilities; 4) arrive at a high likelihood for a diagnosis; 5) decide to provide this case directly to a doctor because the integrated medical platform 245 has no confidence in the diagnosis (statistically), and so forth.

Figure 3:
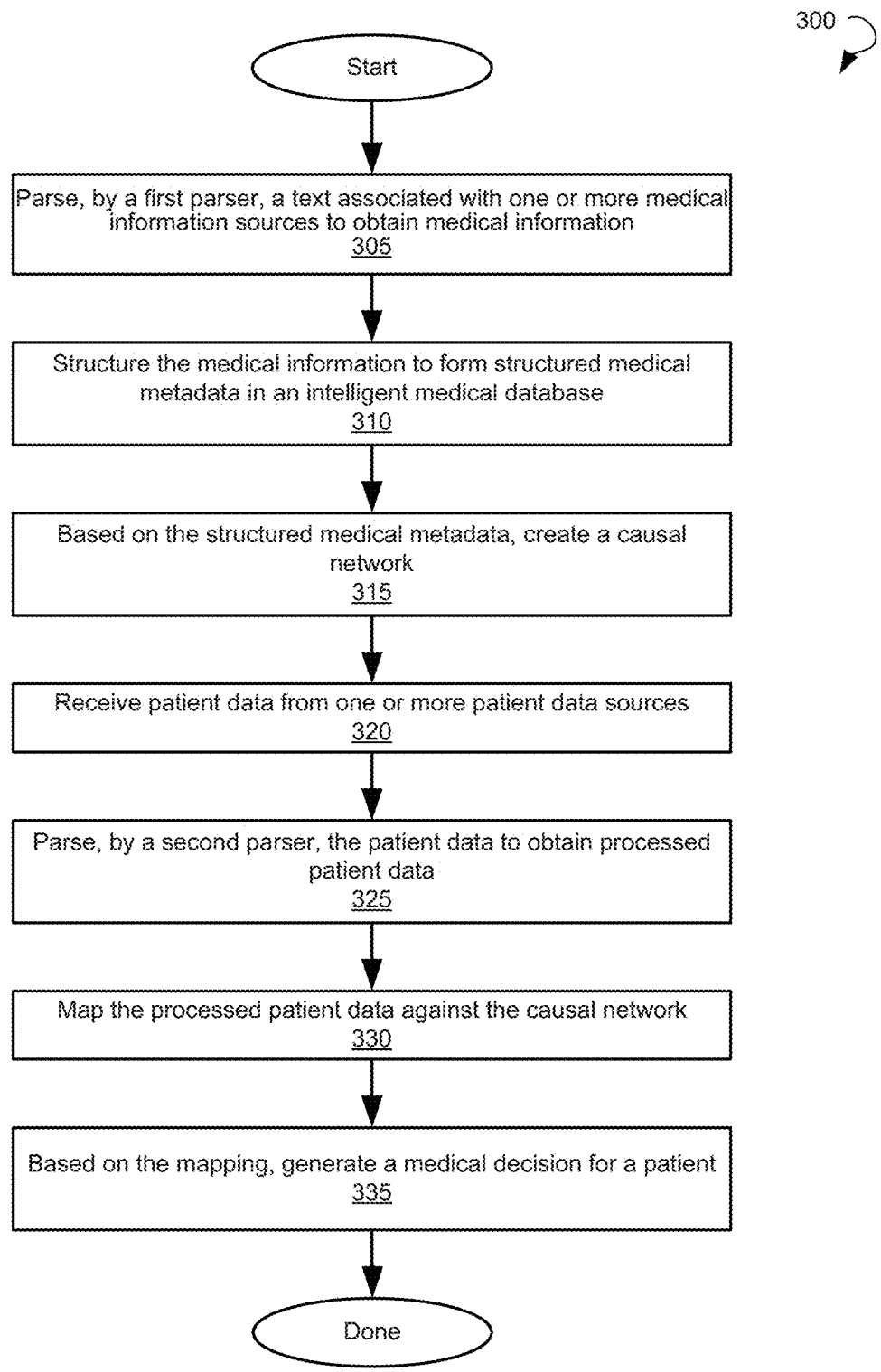
FIG. 3 shows a flow chart illustrating a method for automated medical decision-making.

FIG. 3 is a process flow diagram, illustrating a method 300 for automated medical decision-making, in accordance with an example embodiment. The method 300 may commence with parsing, by a first parser, a text associated with one or more medical information sources to obtain medical information, at operation 305. At operation 310, the medical information may be structured to form structured medical metadata in an intelligent medical database. The structured medical metadata may comprise elements and relationships between the elements. At operation 315, a causal network may be created based on the structured medical metadata.

The method 300 may proceed with receiving patient data from one or more patient data sources, at operation 320, and parsing, by a second parser, the patient data to obtain processed patient data, at operation 325. The processed patient data may further be mapped against the causal network, at operation 330, and, based on the mapping, the medical decision may be generated for a patient, at operation 335.

Figure 4:
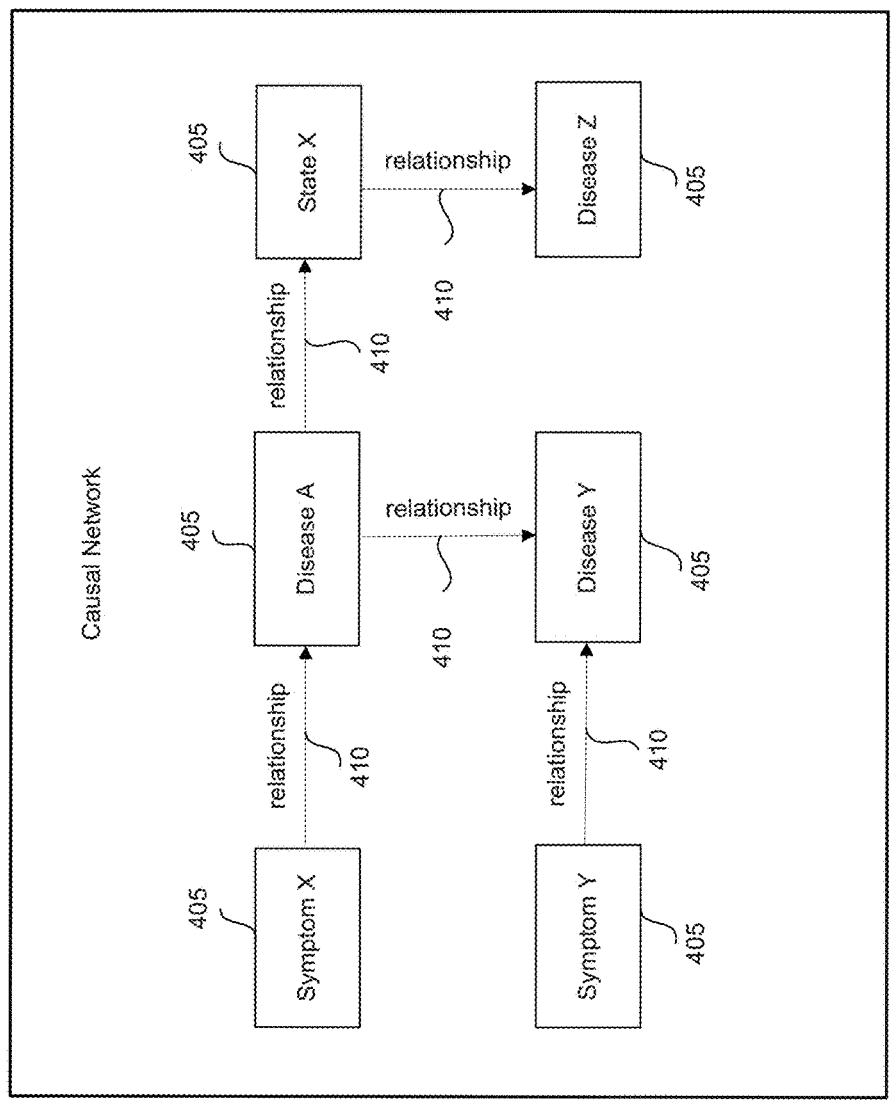
FIG. 4 illustrates a sample causal network.

FIG. 4 is a sample causal network, in accordance with an example embodiment. The causal network 400 is a unique morphology for storing and representing medical knowledge that imbues a unique behavior. The causal network 400 may display a rich set of characteristics, which substantially enhance the clinical gestalt of diagnosis. The causal network 400 may show a potential totality of medical conditions, causes, symptoms, treatments, outcomes, and other relationships, together with the probability distribution of such relationships based on the experience of a population of patients and knowledge embedded into the system for automated medical decision-making 200.

The causal network 400 may be a path connected topological space comprising nodes 405 that represent diseases (Disease A, Disease Y, Disease Z), symptoms (Symptom X, Symptom Y), treatments, states (State X), and the like and relationships 410 between the nodes 405 that are directed dependencies. The relationships 410 in the causal network 400 are statistically weighted, and these weights are unique per patient and even per use for the same patient as a case history for that patient may influence the probabilities of the causal network 400.

The nodes 405 and relationships 410 of the causal network 400 may form a pattern recognition natural language for medical knowledge. The causal network 400 may define medical metadata, the relationships 410 that may exist between metadata elements, and the manner in which they can reference each other.

The structure of the causal network 400 may be characterized by nodes 405 representing the elements of the intelligent medical database 105. The relationships 410 between the nodes 405 may be characterized by relationships among the elements, with the added property that the relationships 410 may be weighted statistically (dynamically) based on patient profile, patient data, and other population data.

In certain example embodiments, building the causal network 400 may include mapping the relationships into an adjacency matrix, and the adjacency matrix may be used to construct a path matrix.

The causal network 400 may represent the ways in which the elements of the intelligent medical database can relate to each other. For example, symptoms may be related to diseases, diseases may be related to outcomes, symptoms may be related to outcomes, diseases may be related to treatments, and so forth.

Furthermore, the nature of the relationships 410 can carry additional information and qualifications, such as likelihood or severity. In the case of likelihood, the relationship 410 can carry a statistical value qualified by different attributes. For example, A might be related to B with a probability of X based on the qualification (a patient is male, over 55 years old, and other attributes).

The likelihood or probability distribution for each of the relationships 410, or for combinations of the relationships 410, may be calculated based on statistical information from a population of patients and from clinical tests. These probability distributions are further enhanced by patient characteristics. In certain example embodiments, the probability may be calculated for any individual patient.

Figure 5:
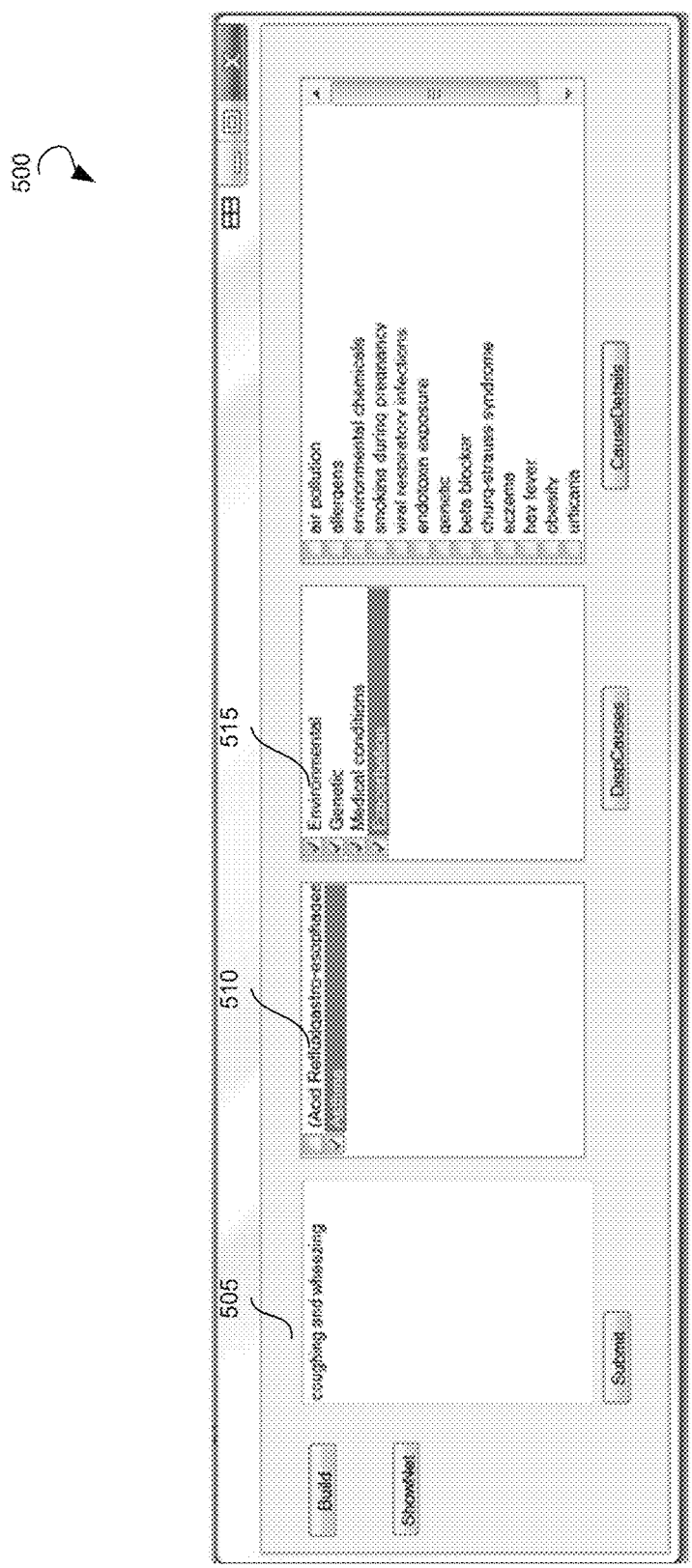
FIG. 5 illustrates a sample screen for a metadata library.

FIG. 5 illustrates a sample screen for a metadata library, in accordance with an example embodiment. The metadata library 500 may include well-structured medical metadata obtained by means of pattern recognition of natural language associated with medical knowledge. The structured medical metadata may include elements, any relationships that may exist between the elements of the medical metadata, and the manner in which the elements can reference each other. In addition, the metadata library 500 may include a number of metadata dictionaries with equivalence classes of medical terms and phrases, so that the elements of the medical metadata that are similar can be treated in a similar manner.

A metadata dictionary may include an equivalence class of terms and phrases associated with a medical lexicon. The equivalency may be important because different standards have different terminologies to describe the same thing. In medication, for example, most patients might have heard of "Nexium" but most physicians probably use "esomeprazole." The metadata dictionary likely exists somewhere and would simply need to be imported, be it from NIH (National Institutes of Health), NICE (National Institute for Clinical Excellence), SNOWMED (Systematized Nomenclature of Medicine), or the index of medical textbooks.

In certain example embodiments, the metadata library 500 may be added with pattern recognition functionality. The pattern recognition may use an equivalence class dictionary of terms and phrases that provides an exhaustive cover of the medical lexicon. Across standards, languages, and differing nomenclatures, two (or more) words or phrases describing the same thing may be placed into the same equivalence class and treated as a single entity. This is important because patients often do not use the same terminology as doctors do, yet the two groups must communicate to achieve an understanding of symptoms and diseases.

In certain example embodiments, the metadata library 500 may be built using a standard set of medical libraries such as Unified Medical Language System (UMLS), SNOWMED CT, and the like.

The metadata library 500 may be constructed with a list of diseases, a set of symptoms that may be observed in a patient suffering from the diseases, a list of tests and tools to confirm or reject a disease as a diagnosis, known relationships between triggers or causes of diseases, such as environmental factors, genetic history, postal codes, workplace factors, patient age/sex/medical history, and the like. The metadata library 500 may additionally comprise relationships to other diseases and conditions, complete with treatment options.

FIG. 5 illustrates a simplified example for the construction of one (symptoms and causes) of the binary relationships for asthma. A static medical metadata and phrase library is used. In this example, patient inputs 505 are coughing and wheezing. The first parser identified two diseases 510: asthma and acid reflux and retrieved all the causes and symptoms 515 associated with the diseases.

The metadata library 500 used may include the following examples:

Disease Metadata: asthma, acid reflux, GERD;

Context Metadata: signs and symptoms, causes, diagnosis, management, treatment;

Symptom Metadata: coughing, wheezing, chest tightness, shortness of breath, heartburn, regurgitation, trouble swallowing, dysphasia, sore throat, odynophagia, pain with swallowing, nausea, chest pain, globus (pharingeus, hystericus), lump in throat;

Causes Metadata: low air quality, allergens, air pollution, environmental chemicals, smoking during pregnancy, formaldehyde exposure, endotoxin exposure, phthalates in PVC, viral respiratory infections, genetic, history of atopic disease, eczema, hay fever, Churg-Strauss syndrome, urticarial, vasculitis, beta blocker, psychological stress, genetic, GERD, obstructive sleep apnea, obesity, rhinosinusitis, Hiatal hernia, Zollinger-Ellison syndrome, hyperkalemia, scleroderma, systemic sclerosis, prednisolone, gallstones, Visceroptosis/Glenard syndrome;

Testing Metadata: spirometry, single-breath diffusing capacity, peak expiratory flow rate, esophageal pH monitoring, barium swallow X-rays, esophageal manometry, esophagogastroduodenoscopy (EGD), short-term treatment with proton-pump inhibitors;

Treatment Metadata: salbutamol (albuterol USAN), ipratropium bromide, anticholinergic bronchodilators, corticosteroids, beta-adrenoceptor agonists, leukotriene antagonists, oxygen, magnesium sulfate, heliox, Intravenous salbutamol, methylxanthines, ketamine, diet, sleeping on the left side, antibiotics, proton-pump inhibitors, PPIs, omeprazole, esomeprazole, pantoprazole, lansoprazole, rabeprazole, gastric H2 receptor blockers, ranitidine, famotidine, cimetidine, antacids, alginic acid, gaviscon, reglan, metoclopramide, prokinetic, sucralfate, carafate, mosapride citrate, 5-HT4 receptor agonist, baclofen, agonist of GABAB receptor, nissen fundoplication, transoral incisionless fundoplication.

Using the metadata library 500 allows improving the quality and effectiveness of personal healthcare, by introducing efficient and intelligent management of patients, while improving the overall quality of care and reducing risks related to incorrect diagnosis, insufficient or excessive tests or treatments, and so forth.

Unlike conventional medical decision support systems, the system for automated medical decision-making 200 provides true integration, from clinical findings to diagnosis to treatment to prognosis and beyond. The integration covers at least a parser, inferential/diagnostic/learning components, decision frameworks, and valuation models. Proper integration of these components may bridge the gap between medical information and medical artificial intelligence.

Figure 6:
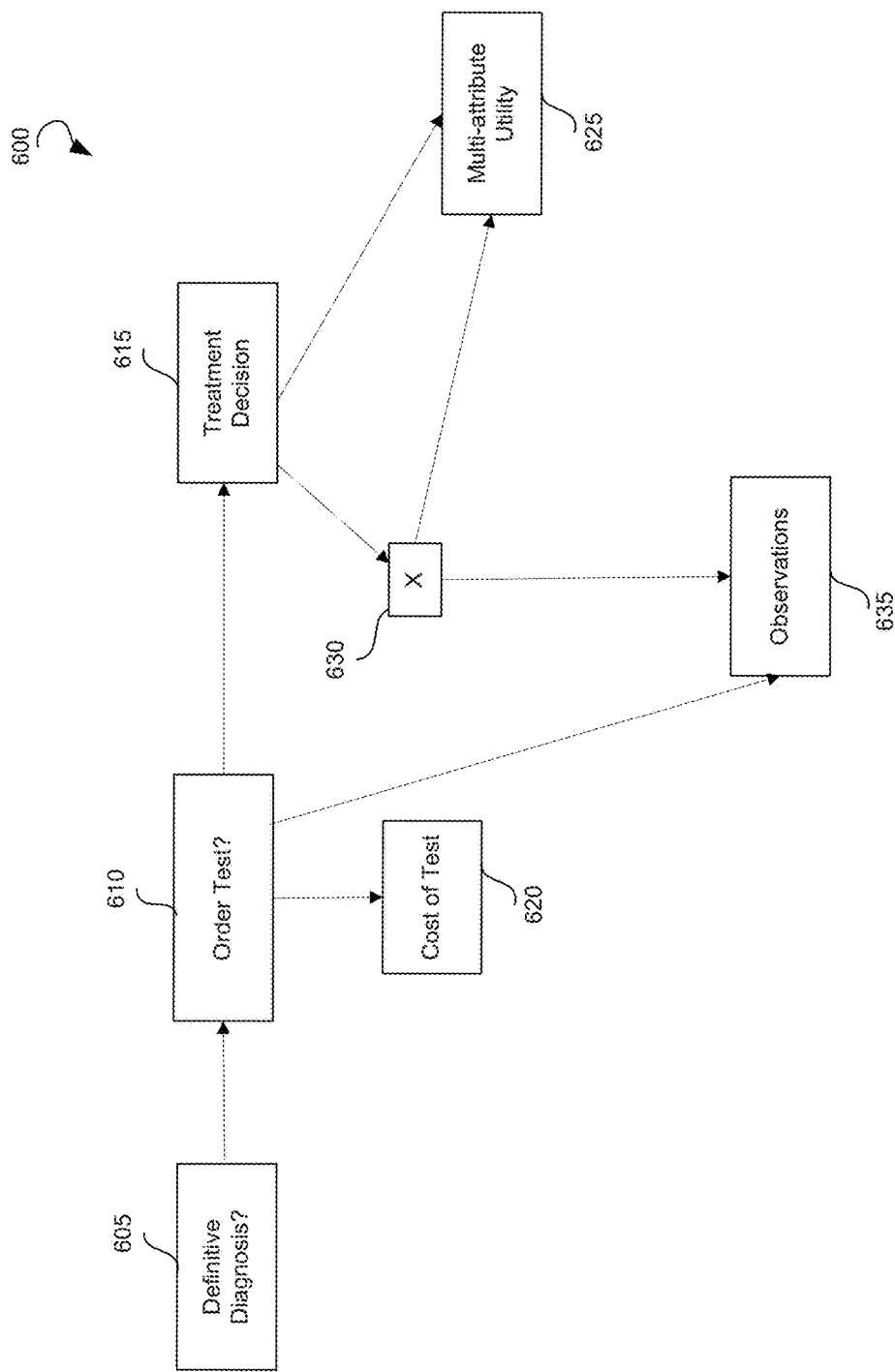
FIG. 6 illustrates a process of decision making using the system for automated medical decision-making.

FIG. 6 illustrates a process 600 of decision making using the system for automated medical decision-making 200. A decision framework of the system for automated medical decision-making 200 consumes output from an inference engine and checks whether the diagnosis is definitive 605. Testing options to support the diagnosis may be evaluated and a test may be ordered 610 or not considering the cost of the test 620. Furthermore, treatment alternatives may be evaluated 615 in terms of efficacy, predicted prognosis, and so forth. Additionally, outcomes of a selected treatment alternative X 630 may be evaluated using multiple criteria by a multi-attribute utility 625 and based on observations 635. The decision framework may screen first for high risk situations (e.g., life-threatening) and low risk contexts (e.g., alarm system).

In some embodiments, the decision framework may capture and represent information about patient, doctor, or medical organization preferences, estimated costs for alternative treatment options, and further related information. Such information allows introduction of further aspects in the decision process.

The system for automated medical decision-making 200 brings a valuation capability to its architecture and design. The health status of a patient is presumed to be multi-attributed; therefore, the system 200 characterizes or describes multi-attribute health states as $y=(y_1, \ldots, y_n)$. For example, a two-attribute case, $y=(y_1; y_2)$, may be considered for evaluation treatment options for ovarian cancer. In this case, $y_1$ may be identically equal to radiation side-effects, and $y_2$ may be identically equal to fertility.

The system for automated medical decision-making 200 is directed at end-to-end patient management to embrace patient management lifecycle (symptoms, diagnostics, testing, treatment plan, anticipated prognosis, and patient tracking), natural language parsing of patient symptoms (almost instantaneous machine interpretation of patient statements and case history), and sophisticated causal mapping of relevant medical knowledge and information (intelligence may represent relevant substrates). These elements can be considered an intelligent infrastructure (absent any data) onto which medical information can be mapped and learned. A patient substrate is defined as a sub-net of the architecture, together with probabilistic characterizations of likelihoods associated with individual nodes and paths in the network. Using the system for automated medical decision-making 200, complete electronic handling of patients may be implemented, including consuming voice, text, and laboratory data, performing diagnostics, automatically filling out template forms, having the control and audit mechanisms in place, statistical and other risk based inference models that mitigate risk to patient, doctor, insurer, and so forth.

Figure 7:
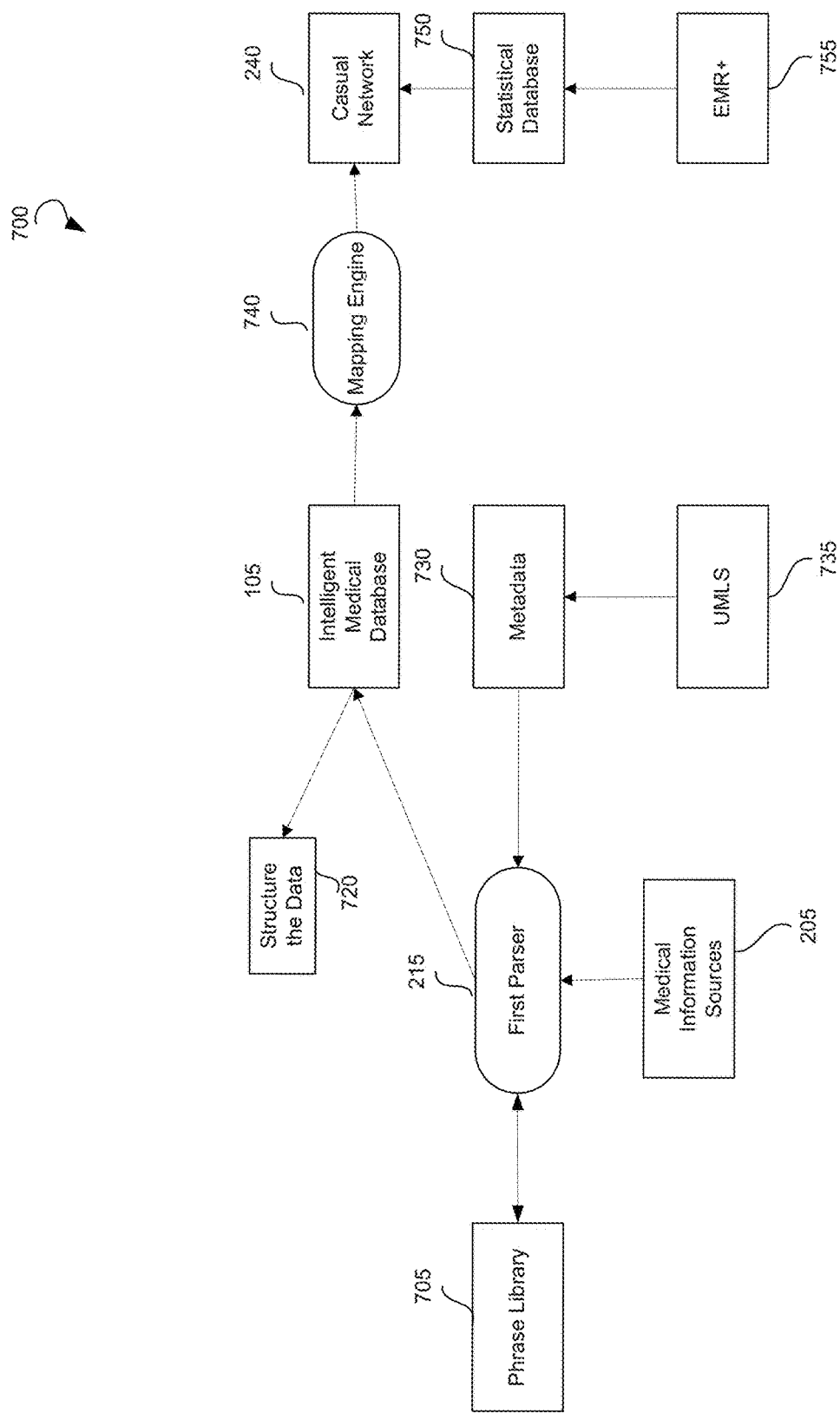
FIG. 7 illustrates creating a patient substrate using the system for automated medical decision-making.

FIG. 7 illustrates creating patient substrate 700 using the system for automated medical decision-making 200. Using a phrase library 705, medical information sources 205, and medical terminology systems (e.g., UMLS) 735, the first parser 215 may provide medical information and metadata 730 to the intelligent medical database 105. The intelligent medical database 105 may structure the medical data 720 to form structured medical metadata in intelligent medical database 105 and eventually create a casual network. Patient data may be received, for example, from EMR 755 and stored in a statistical database 750. A mapping engine 740 may map patient data to the causal network 240 to receive the patient substrate.

Figure 8:
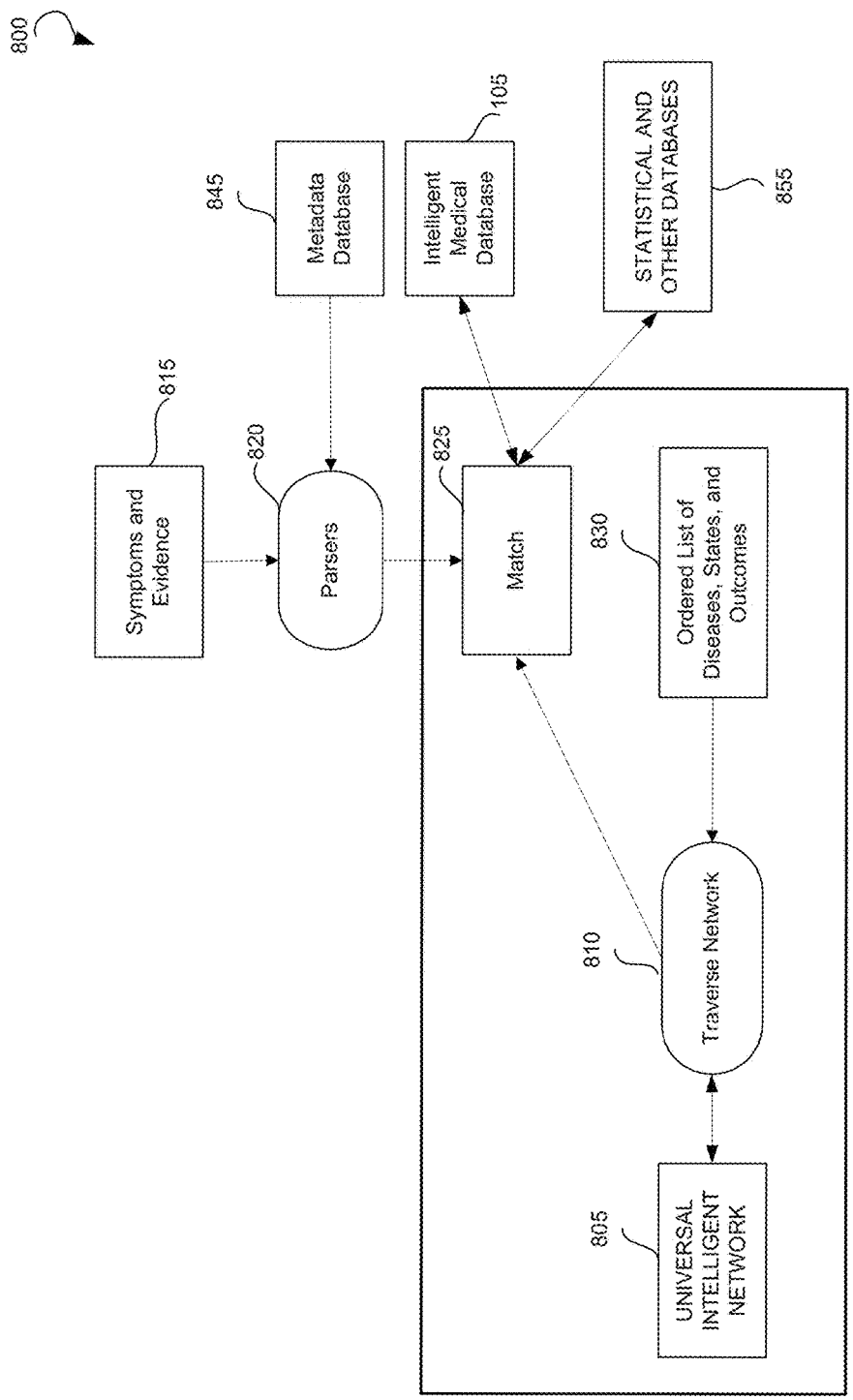
FIG. 8 illustrates finding a match based on symptoms and evidences.

FIG. 8 illustrates a process 800 of finding a match 825 based on symptoms and evidences 815. Parsers 820 provide medical data from a metadata database 845 and symptoms and evidences 815. Using the medical data, a match is determined in a universal intelligent network 805 by traversing the network 810, and corresponding information is received from an ordered list of diseases, states, and outcomes 830. Further information associated with the match 825 may be received from the intelligent medical database 105 as well as statistical and other databases 855.

Figure 9:
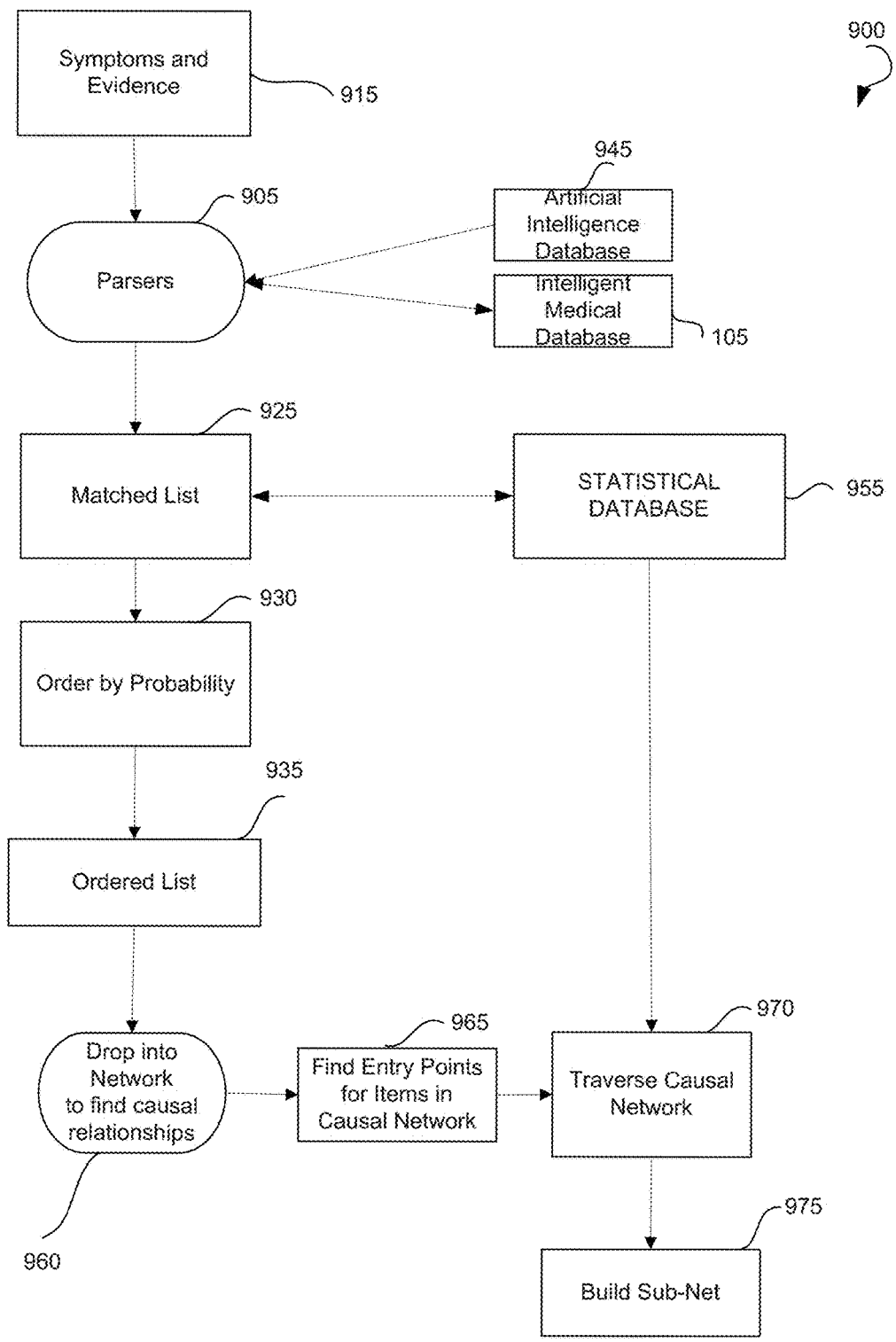
FIG. 9 illustrates a more detailed procedure for finding a match based on symptoms and evidences.

In more detail, this procedure is shown by FIG. 9. Procedure 900 includes receiving symptoms and evidence 915 by parsers 905. The parsers 905 may additionally receive related information from artificial intelligence database 945 and intelligent medical database 105. Further, symptoms and evidence 915 may be matched with diseases, states, and outcomes using the statistical database 955 to obtain a matched list 925. The matched list 925 may be ordered by probability 930 to obtain an ordered list 935, which is dropped into a causal network to find causal relationships 960. Entry points for items in the causal network may be found 965. Then, the causal network may be traversed 970 and a sub-net may be built 975.

Figure 10:
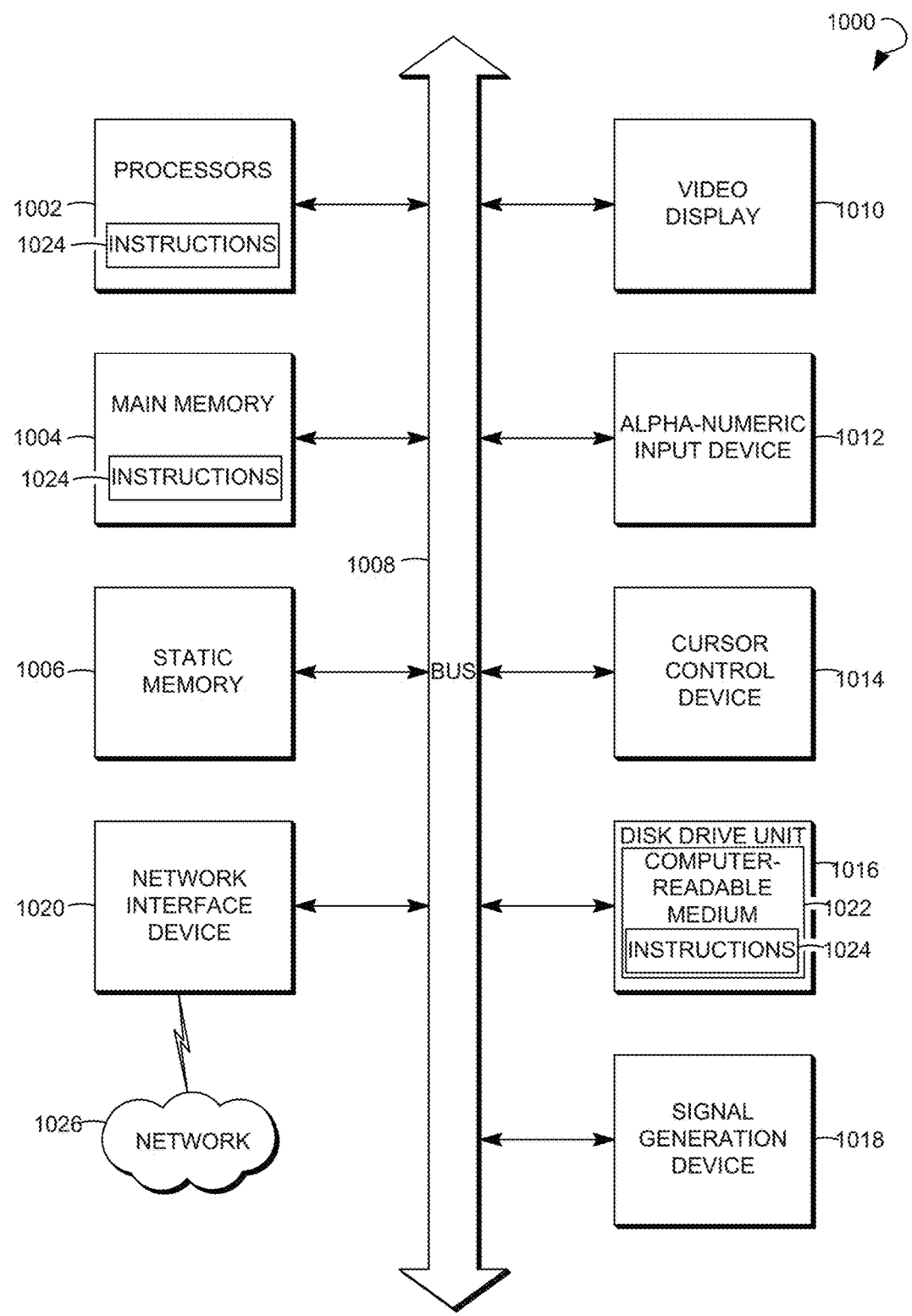
FIG. 10 illustrates a diagrammatic representation of an example machine in the form of a computer system within which a set of instructions for causing the machine to perform any one or more of the methodologies discussed herein is executed.

FIG. 10 illustrates a diagrammatic representation of an example machine in the form of a computer system within which a set of instructions for causing the machine to perform any one or more of the methodologies discussed herein is executed. A computer system 1000 may include a set of instructions for causing the machine to perform any one or more of the methodologies discussed herein may be executed. In various example embodiments, the machine operates as a standalone device or may be connected (e.g., networked) to other machines. In a networked deployment, the machine may operate in the capacity of a server or a client machine in a server-client network environment, or as a peer machine in a peer-to-peer (or distributed) network environment. The machine may be a personal computer (PC), a tablet PC, a set-top box (STB), a tablet computer, a cellular telephone, a smartphone, a portable music player (e.g., a portable hard drive audio device such as a Moving Picture Experts Group Audio Layer 3 (MP3) player), a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1000 includes a processor or multiple processors 1002 (e.g., a central processing unit (CPU), a graphics processing unit (GPU), or both), a main memory 1004, and a static memory 1006, which communicate with each other via a bus 1008. The computer system 1000 may further include a video display unit 1010 (e.g., a liquid crystal display (LCD) or a cathode ray tube (CRT)). The computer system 1000 may also include an alphanumeric input device 1012 (e.g., a keyboard), a cursor control device 1014 (e.g., a mouse), a disk drive unit 1016, a signal generation device 1018 (e.g., a speaker), and a network interface device 1020.

The disk drive unit 1016 includes a computer-readable medium 1022, on which is stored one or more sets of instructions and data structures (e.g., instructions 1024) embodying or utilized by any one or more of the methodologies or functions described herein. The instructions 1024 may also reside, completely or at least partially, within the main memory 1004 and/or within the processors 1002 during execution thereof by the computer system 1000. The main memory 1004 and the processors 1002 may also constitute machine-readable media.

The instructions 1024 may further be transmitted or received over a network 1026 via the network interface device 1020 utilizing any one of a number of well-known transfer protocols (e.g., HyperText Transfer Protocol (HTTP)).

While the computer-readable medium 1022 is shown in an example embodiment to be a single medium, the term "computer-readable medium" should be taken to include a single medium or multiple media (e.g., a centralized or distributed database and/or associated caches and servers) that store the one or more sets of instructions. The term "computer-readable medium" shall also be taken to include any medium that is capable of storing, encoding, or carrying a set of instructions for execution by the machine and that causes the machine to perform any one or more of the methodologies of the present application, or that is capable of storing, encoding, or carrying data structures utilized by or associated with such a set of instructions. The term "computer-readable medium" shall accordingly be taken to include, but not be limited to, solid-state memories, optical and magnetic media, and carrier wave signals. Such media may also include, without limitation, hard disks, floppy disks, flash memory cards, digital video disks, random access memory (RAM), read only memory (ROM), and the like.

The example embodiments described herein may be implemented in an operating environment comprising software installed on a computer, in hardware, or in a combination of software and hardware.

Thus, systems and methods for automated medical decision-making have been described. Although embodiments have been described with reference to specific example embodiments, it will be evident that various modifications and changes may be made to these embodiments without departing from the broader spirit and scope of the system and method described herein. Accordingly, the specification and drawings are to be regarded in an illustrative rather than a restrictive sense.

What is claimed is:

1. A computer-implemented method for automated medical decision-making that is customized for a patient, the method comprising:

parsing, by a first parser, unstructured natural language text from a plurality of authoritative medical sources to obtain authoritative medical information, the parsing further comprising using:
a metadata dictionary; and
pattern recognition artificial intelligence to interpret at least one word or phrase in the obtained unstructured text from the plurality of authoritative medical sources to appropriately place the at least one word or phrase within one or more backend data structures of an intelligent medical database of an electronic integrated medical platform;

structuring, by a processor, the authoritative medical information to form structured medical metadata in an intelligent medical database, wherein the structured medical metadata comprises a plurality of medical elements and relationships between the plurality of medical elements, the intelligent medical database forming a part of the electronic integrated medical platform;

based on the structured medical metadata, creating, by the processor, a causal computing network that is customized for the patient, wherein the causal computing network includes a topological space comprising:
a plurality of nodes, each of the plurality of nodes representing at least one of the plurality of medical elements of the structured medical metadata; and
at least one link between a pair of nodes, each of the at least one link representing a relationship between the pair of nodes;

traversing the causal computing network to identify and create a sub-network from the causal computing network for at least one patient symptom from the obtained patient data;

generating, based on the created sub-network, at least one of a predicted disease, predicted condition, or predicted state of the patient, and a corresponding probability of each of the generated at least one predicted disease, predicted condition, or predicted state; and presenting the at least one predicted disease, predicted condition, or predicted state of the patient and the corresponding probability of each of the generated at least one predicted disease, predicted condition, or predicted state to the patient via a graphical user interface of a patient computing device in communication with the electronic integrated medical platform.

2. The method of claim 1, wherein the medical elements of the structured medical metadata include one or more of the following: a disease, a state, a cause, a symptom, a treatment, a test, an effect, an outcome, and an outlier.

3. The method of claim 1, further comprising: weighting statistically, based on the patient data, the relationships between the elements of the structured medical metadata.

4. The method of claim 1, further comprising providing automated medical decision-making.

5. The method of claim 1, wherein a second parser further comprises: processing the patient data using an inference model and pattern recognition.

6. The method of claim 1, further comprising: retrieving, interpreting, and collating, by one or more grammar independent natural language parsers, the medical information from the authoritative medical sources.

7. A system for automated medical decision-making that is customized for a patient, the system comprising:

a first natural language parser configured to:
obtain and parse unstructured text from a plurality of authoritative medical sources to obtain authoritative medical information, the parsing further comprising using:
a metadata dictionary; and
pattern recognition artificial intelligence to interpret at least one word or phrase in the obtained unstructured text from the plurality of authoritative medical sources to appropriately place the at least one word or phrase within one or more backend data structures of an intelligent medical database of an electronic integrated medical platform;

a second natural language parser, different from the first natural language parser, the second natural language parser configured to:
obtain and parse important patient data from a plurality of patient data sources, the important patient data comprising at least two of: symptoms, diagnosed diseases, gender, and age;
disregard unimportant patient data obtained;
wherein the second natural language parser further uses:
an inference model; and
pattern recognition artificial intelligence to identify at least one patient symptom and severity of the at least one patient symptom from the obtained patient data; and a processor of the electronic integrated medical platform, the processor in communication with the first natural language parser and the second natural language parser, the processor being configured to:
structure medical information from the parsed authoritative medical sources and from the parsed patient data sources to form structured medical metadata in the intelligent medical database that is customized for the patient, wherein the structured medical metadata comprises:
a plurality of medical elements and relationships between the plurality of medical elements, the intelligent medical database forming a part of the integrated medical platform;
utilize the structured medical metadata to create a causal computing network that is customized for the patient, wherein the causal computing network includes a topological space comprising:
a plurality of nodes, each of the plurality of nodes representing at least one of the plurality of medical elements of the structured medical metadata; and
at least one link between a pair of nodes, each of the at least one link representing a relationship between the pair of nodes;
traverse the causal computing network to identify and create a sub-network from the causal computing network for at least one patient symptom from the obtained important patient data;
generate, based on the created sub-network, at least one of a predicted disease, predicted condition, or predicted state of the patient, and a corresponding probability of each of the generated at least one predicted disease, predicted condition, or predicted state; and
present the at least one predicted disease, predicted condition, or predicted state of the patient and the corresponding probability of each of the generated at least one predicted disease, predicted condition, or predicted state to the patient via a graphical user interface of a patient computing device in communication with the electronic integrated medical platform.

8. The system of claim 7, wherein the medical elements of the structured medical metadata include one or more of the following: a disease, a state, a cause, a symptom, a treatment, a test, an effect, an outcome, and an outlier.

9. The system of claim 7, wherein the relationships between the plurality of medical elements of the structured medical metadata are weighted statistically based on the patient data in a manner that is unique for each patient.

10. The system of claim 7, wherein the first parser and the second parser include one or more grammar independent natural language parsers, the one or more grammar independent natural language parsers configured to retrieve, interpret, and collate the medical information from the plurality of authoritative medical sources.

11. The system of claim 7, wherein the metadata dictionary includes an equivalence class of terms and phrases associated with a medical lexicon.

12. The system of claim 7, wherein the metadata dictionary is captured using a bioinformatics ontology.

13. The system of claim 7, wherein one of the plurality of patient data sources includes patient input in a form of a natural language.

14. The system of claim 7, wherein the patient data includes a text or a speech converted into text.

15. A system for automated medical decision-making, the system comprising:
a first parser configured to parse unstructured text from a plurality of authoritative medical sources to obtain authoritative medical information, the parsing further comprising using:
pattern recognition artificial intelligence to interpret at least one word or phrase in the obtained unstructured text from the plurality of authoritative medical sources to appropriately place the at least one word or phrase within one or more backend data structures of an intelligent medical database of an electronic integrated medical platform;
a second parser configured to parse patient data from a plurality of patient data sources, important patient data comprising at least two of: symptoms, diagnosed diseases, gender, and age;
wherein the second parser further uses:
pattern recognition artificial intelligence to identify at least one patient symptom and severity of the at least one patient symptom from the obtained patient data; and
a processor of the electronic integrated medical platform, the processor in communication with the first parser and the second parser, the processor being configured to:
structure the medical information to form structured medical metadata in the intelligent medical database, wherein the structured medical metadata comprises elements and relationships between the elements, wherein the elements of the structured medical metadata include one or more of the following: a disease, a state, a cause, a symptom, a treatment, a test, an effect, an outcome, and an outlier, the intelligent medical database forming a part of a framework;
create, based on the structured medical metadata, a causal network, wherein the causal network includes a topological space with nodes and links between the nodes, wherein the nodes represent the elements of the structured medical metadata and the links represent the relationships between the elements, the relationships between the elements of the structured medical metadata being weighted statistically based on the patient data;
receive the patient data from one or more patient data sources;
map the parsed patient data against the causal network, the mapping performed against the framework; and generate, based on the mapping, a medical decision for the patient, the medical decision including a treatment.

16. The system of claim 7, wherein the first natural language parser is further configured to: read, decode, and update medical information from an authoritative medical source of the plurality of authoritative medical sources; and
the processor of the electronic integrated medical platform is further configured to: update at least one link between a pair of nodes in the causal computing network, based on the updated medical information from the first natural language parser.

17. The system of claim 7, further comprising:
generating, based on the created sub-network, at least one treatment plan for the patient, and a likelihood of success of the at least one treatment plan for the patient.

18. The system of claim 7, wherein the at least one predicted disease, predicted condition, or predicted state of the patient is presented on the graphical user interface of the patient computing device in a ranked order, the ranked order determined based on the intelligent medical database that is customized for the patient.

\* \* \* \* \*